(12) United States Patent
Omberg

(10) Patent No.: US 10,624,782 B2
(45) Date of Patent: Apr. 21, 2020

(54) CONTACT LENS MANIPULATOR ASSEMBLY AND A METHOD THEREOF

(71) Applicant: DK Vision AS, Oslo (NO)

(72) Inventor: Corrine Jacqueline Omberg, Oslo (NO)

(73) Assignee: DK Vision AS, Oslo (NO)

( * ) Notice: Subject to any disclaimer, the term of this patent is extended or adjusted under 35 U.S.C. 154(b) by 0 days.

(21) Appl. No.: 16/331,184

(22) PCT Filed: Sep. 7, 2017

(86) PCT No.: PCT/NO2017/050219
§ 371 (c)(1),
(2) Date: Mar. 7, 2019

(87) PCT Pub. No.: WO2018/048309
PCT Pub. Date: Mar. 15, 2018

(65) Prior Publication Data
US 2019/0274879 A1    Sep. 12, 2019

(30) Foreign Application Priority Data

Sep. 7, 2016 (NO) .................................. 20161421

(51) Int. Cl.
*A61F 9/00* (2006.01)
(52) U.S. Cl.
CPC ................. *A61F 9/0061* (2013.01)
(58) Field of Classification Search
CPC ..................................... A61F 9/0061
USPC ................................. 294/1.2, 210
See application file for complete search history.

(56) References Cited

U.S. PATENT DOCUMENTS

| 4,037,866 A | | 7/1977 | Price | |
| 4,093,291 A | * | 6/1978 | Schurgin | A61F 9/0061 294/1.2 |
| 4,126,345 A | | 11/1978 | List | |
| 4,221,414 A | * | 9/1980 | Schrier | A61F 9/0061 294/1.2 |
| 4,326,742 A | * | 4/1982 | Ingram | G02C 5/005 294/1.2 |
| 4,750,771 A | * | 6/1988 | Emmett | A61F 9/0061 15/104.001 |
| 4,753,470 A | | 6/1988 | Menard | |

(Continued)

FOREIGN PATENT DOCUMENTS

CN        203539527 U    4/2014

OTHER PUBLICATIONS

N. Rex Ghormley, How Modulus Affects Soft Contact Lenses, Nov. 1, 2005, https://www.clspectrum.com/issues/2005/november-2005/how-modulus-affects-soft-contact-lenses (Year: 2005).*

(Continued)

*Primary Examiner* — Stephen A Vu
(74) *Attorney, Agent, or Firm* — Greenberg Traurig, LLP; David J. Dykeman; Jaime Burke

(57) ABSTRACT

A contact lens manipulator assembly comprising a main manipulator body (7) arranged to support a lens applicator (2) in one end and a pincer (3) in an opposite end of the main manipulator body (7) is disclosed. The contact lens manipulator comprises further a contact lens fetcher (1) arranged releasable in a longitudinal bore (6) of the main manipulator body (7).

16 Claims, 12 Drawing Sheets

(56) References Cited

U.S. PATENT DOCUMENTS

| | | | | |
|---|---|---|---|---|
| D296,791 S | * | 7/1988 | Kolack | 294/1.2 |
| 4,986,586 A | * | 1/1991 | Eilrich | A61F 9/0061 |
| | | | | 294/1.2 |
| 5,941,583 A | | 8/1999 | Raimondi | |
| 2014/0159397 A1 | * | 6/2014 | Saitoh | A61F 9/0061 |
| | | | | 294/1.2 |

OTHER PUBLICATIONS

International Search Report in PCT International Application No. PCT/NO2017/050219 dated Jan. 3, 2018.
Norwegian Search Report in Norwegian Application No. 20161421 dated Apr. 7, 2017.

* cited by examiner

1:1

2:1

3/4 view

Bottom view

3/4 view

Left view

Front/back view

Right view

3/4 view

Top view

3/4 view

3/4 view

Bottom view

3/4 view

Left view

Front/back view

Right view

3/4 view

Top view

3/4 view

CONTACT LENS MANIPULATOR ASSEMBLY AND A METHOD THEREOF

CROSS-REFERENCE AND CLAIM OF PRIORITY TO RELATED APPLICATIONS

This application is a U.S. national phase application of PCT International Patent Application No. PCT/NO2017/050219, filed on Sep. 7, 2017, which claims the benefit of and priority to Norwegian patent application no. 20161421, filed Sep. 7, 2016, each of which are hereby incorporated by reference in their entireties.

FIELD OF THE INVENTION

The present invention is related to a contact lens manipulator, and especially to a contact lens manipulator comprising a combined assembly of a contact lens applicator and a contact lens removal device, and a method thereof.

BACKGROUND OF THE INVENTION

Contact lenses are widely used. However, placing and removing a contact lens from a human eyeball usually requires some training. A main challenge using contact lenses is to avoid eye infections due to bacterial or virus contamination of the contact lenses, for example from contact with fingers when manually placing or removing contact lenses. Disposable lenses are common which may reduce the contamination risk and lenses intended for reuse are usually stored in a storage box with disinfection fluids disinfecting the lenses in the periods between use. Another more technical challenge for users may arise when the contact lenses are soft contact lenses, which may be more difficult to handle than a rigid body of a contact lens.

However, the potential risk of infectious contamination of contact lenses is high when removing a contact lens, either a disposable lens or an ordinary contact lens, from the storage box and applying a lens onto the eyeball surface. Any contact between fingers and the contact lens body provides a risk of contamination of the lens body.

In prior art there are examples of devices that help a user when manipulating a contact lens into contact with an eyeball, and when removing the contact lens from the eyeball.

U.S. Pat. No. 4,126,345 A discloses a device handling soft contact lenses comprising a pair of resilient pincer arms, each arm having one end mutually interconnected and a free end spaced apart from the other free end. A lens cup is attached to the interconnected arm ends and is shaped for receiving and holding a soft contact lens. The free end of each pincer arm includes a connected soft tip, which extends outwardly therefrom, and is constructed of a resilient, flexible material, and has a terminal surface shaped for frictionally engaging an outer surface of a soft contact lens. The arms are interconnected for positioning the tips on opposing sides of the lens when the soft contact lens is positioned on the eye of a wearer, whereby convergence of the arms folds the lens between the tips for removal of the lens from the eye.

U.S. Pat. No. 4,221,414 A discloses a device for the insertion and removal of soft contact lenses comprising a bifurcated member having a pair of flexible arms extending from the main body and contact lens gripping surfaces attached to the ends of each of the flexible arms. The angular tips are constructed and shaped at the precise angle necessary so that, when placed against a contact lens, the lens may be flexed and removed from the eyeball, or, inversely, easily placed on the eyeball.

WO 9304648 A1 discloses an applicator (10) which is useful for placing a contact lens (18) on an eye of a wearer. The applicator (10) comprises an elongate hollow body (11) open at both ends (15, 16). The inner surface of the body (11) defines a concave surface (17) adapted to receive the lens (18) at one end (15) and a bore (13) which extends from the concave surface (17) to the other end (16). A plunger (12) is received in the bore (13) from the other end (16). Movement of the plunger (12) towards the concave surface (17) propels a contact lens (18) from the concave surface (17) onto the eyeball.

Prior art discloses tools with respect to the action of removing a soft contact lens and the action of placing a soft contact lens on the eye of a user. Even though this may be functional stand-alone units, it would be beneficial to have a common tool, or common tool assembly, improving an easy secure and sterile removal and placement of soft contact lenses.

The eye is largely shaped as a ball and has consequently a convex shape. When placing a contact lens onto an eye it is required that the contact lens substantially follows the contour of the cornea. The forces holding a lens in its proper location on the cornea are the suction forces created between the cornea and the inside of the contact lens, i.e. the concave surface of the contact lens. When removing a contact lens it is necessary to overcome this suction effect and this may be accomplished by removing the suctioning action between the contact lens and the cornea by introducing air between these two elements. For soft contact lenses this may be achieved by making a crease in the contact lens to introduce air between the contact lens and the cornea and thus to even out the pressure between the ambient air and the space between the cornea and the inside surface of the contact lens.

On account of this situation it is required that a contact lens is placed with its concave surface facing the cornea, and this requires that a tool placing the contact lens onto the eye introduces the contact lens to the cornea with its concave surface facing the cornea end its convex surface facing outwards. Based on this requirement, the orientation of the contact lens when collected from its resting position in its holder (when not in use) is of importance. If the contact lens is located in its holder with its convex surface facing upwards (towards the user), the applicator part of the device according to the invention may be used directly for collecting the contact lens and placing it onto the eye. Oppositely, when the contact lens is located in its holder with its concave surface facing upwards, it is required that an intermediate part of an applicator is used for bringing the contact lens with its concave surface facing the eye when applied on the applicator.

OBJECT OF THE INVENTION

In particular, it may be seen as an object of the present invention to provide a contact lens manipulator assembly comprising respectively operational units being assembled into a common operational assembly providing an operational environment with enhanced secure, safe and contamination-free operation when applying a contact lens onto a human eyeball and when removing a contact lens body from a human eyeball.

It is a further object of the present invention to provide an alternative to prior art.

SUMMARY OF THE INVENTION

Thus, the above-described object and several other objects are intended to be obtained in a first aspect of the invention by providing a contact lens manipulator assembly comprising a main manipulator body arranged with a lens applicator in a first end of the main manipulator body, and a pincer in a second end of the main manipulator body opposite the first end, wherein a lens-fetching device comprising an outwardly shaped hemisphere part (1a) located on a first end of a shaft, wherein a second end of the shaft opposite the hemisphere-shaped part is adapted to be releasable inserted into a bore (6) arranged in a longitudinal direction of the main manipulator body, wherein the bore is arranged from a centre point on a curved surface of the lens applicator facing outwardly through the main manipulator body to a centre point on a joining surface of the main manipulator body in between a first gripping arm and a second gripping arm (3b) of the pincer.

The above-described objects are further obtained by a method of placing a contact lens onto a human eyeball comprising using a contact manipulator assembly according to the present invention, wherein a user when placing a contact lens onto an eyeball performs the following steps:

removing a lens-fetching device from a bore arranged in a longitudinal direction of main manipulator body by pushing a shaft of the lens-fetching device out of the bore by manually pushing the shaft from a pincer side of the main manipulator body, when the shaft (1b) is sufficiently extending out away from a lens applicator, gripping the shaft of the lens-fetching device with at least two fingers of a first hand without contacting any surface of the main manipulator body and a hemisphere-shaped part of the lens-fetching device with the fingers, or any other fingers, open a storage box housing a contact lens body to be applied onto an eyeball, place the hemisphere-shaped part of the lens-fetching device in contact with a surface of the contact lens facing upwards inside the storage box, remove the contact lens from the storage box with the lens-fetching device, gripping the main manipulator body with a second hand, and transferring the contact lens body from the hemisphere-shaped part of the lens-fetching device kept in the first hand towards a surface of the lens applicator part of the main manipulator body for ensuring a correct curvature of the lens when applied to the eye, apply the lens applicator part in operational contact with the eyeball receiving the lens and release the lens onto the surface of the eyeball, and optionally assemble and store the contact lens manipulator assembly in a storage container.

The described objects above are further obtained by a method of removing a contact lens from a human eyeball, comprising using a contact manipulator assembly according to the present invention, wherein a user when removing a contact lens from the eyeball performs the following steps:

removing a lens-fetching device from a bore arranged in a longitudinal direction of a main manipulator body by pushing a shaft of a lens-fetching device out of the bore by manually pushing the shaft from a pincer side of the main manipulator body, when the shaft is sufficiently extending out away from a lens applicator, gripping the shaft of the lens-fetching device with at least two fingers of a first hand without contacting any surface of the main manipulator body and the hemisphere-shaped part of the lens-fetching device with the fingers, or any other fingers, open a storage box to be used when storing the contact lens body to be removed from the eyeball, gripping the main manipulator body with a second hand and place the pincer in operational contact with the contact lens on the eyeball, and remove the contact lens from the eyeball with the pincer, and transfer the contact lens body from the pincer to the hemisphere-shaped part of the lens-fetching device kept in the first hand, placing and releasing the contact lens body inside the storage box and close the box, and optionally assemble and store the contact lens manipulator assembly in a storage container, or optionally place the used contact lens body in a dustbin.

The individual aspects and/or examples of embodiments of the present invention may each be combined with any of the other aspects and/or examples of embodiments. These and other aspects of the invention will be apparent from the following description with reference to the described embodiments.

BRIEF DESCRIPTION OF THE FIGURES

The contact lens manipulator assembly according to the present invention will now be described in more detail with reference to the accompanying figures. The figures illustrate examples of embodiments of the present invention and are not to be construed as being limited to other possible embodiments falling within the scope of the attached set of claims.

DETAILED DESCRIPTION OF AN EMBODIMENT OF THE PRESENT INVENTION

Figure 1:
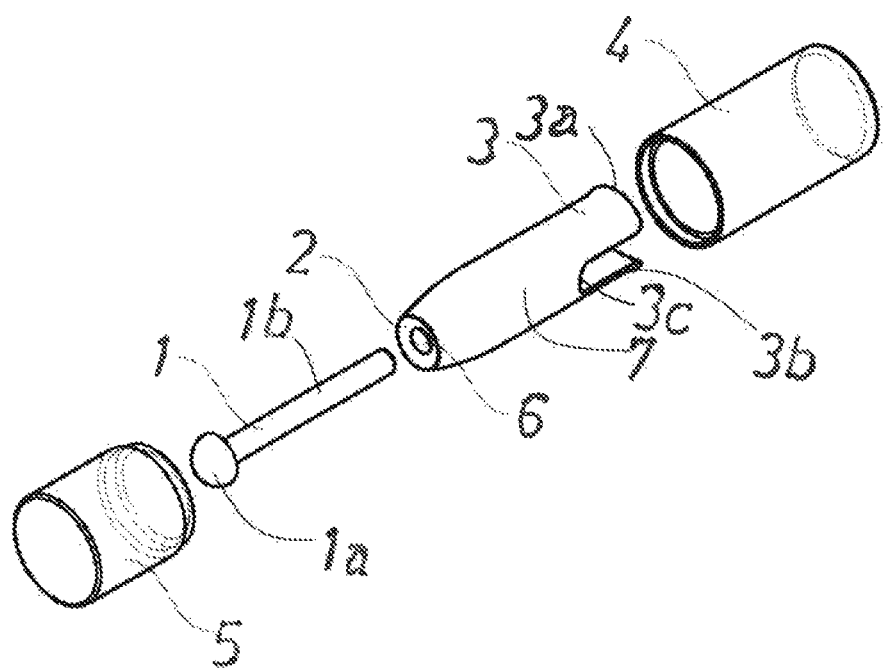
FIG. 1 illustrates an example of embodiment of the present invention.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or steps. In addition, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims may possibly be advantageously combined and the mentioning of these features in different claims does not exclude that a combination of features is not possible and advantageous.

Contact lenses are manufactured with a curved first inner surface intended to engage the outer surface of the eyeball when used. A second outer surface of the lens body is adapted with a curvature providing optical correction of the wearer's eyesight as known to a person skilled in the art.

Distribution of contact lenses to consumers is inside sterile boxes. It is common to let contact lenses rest against an indent being curved downwards inside the lens storage box, wherein the second outer surface of the contact lens is facing downwards inside the indent, wherein the indent curvature is adapted to the shape of the second outer surface of the contact lens body. The first inner concave surface of the contact lens is facing upwards. This is the surface engaging the eyeball when placed onto the eye of a user and is therefore the surface with a high contamination risk. However, the opposite side of the contact lens represents an external surface of the lens when worn and may also be prone to contamination. It is also in contact with the internal surface of the eyelid and may also represent a source for microorganisms being harmful to the eye of the user. Consequently this surface should also be treated as aseptically as possible.

Prior art disclose examples of flexible arms (pincers) that can be used to grip the contact lens body. However, due to the common orientation of the lens body in the storage and shipment boxes, the flexible arms would remove the lens body in a position which, when applied directly onto an eyeball, would let the second outer surface of the lens body be faced towards the eyeball. Therefore, using a pincer-like tool would not function without an intermediate step of turning the lens body around before applying the lens body onto the eyeball thereby letting the first surface of the lens body engaging the eyeball surface. This operation is difficult without contacting the lens body with for example fingers.

The human eye is a sensitive organ and any damage to the human eye lens from any tool could degrade the visual quality of the human eye. Therefore, any design of an applicator and a remover device of contact lenses must take into account the risk of mechanically damaging an eyeball during operation of the tool.

Further, operating an application and removal device should not obstruct the user's view of the operation of a tool a user is performing on him or herself. If there were visual obstructions from the tool body itself, the user would apply or remove the contact lens more or less blinded. Then the risk of mechanically damaging the human eyeball (i.e. human eye lens) increases. Further correct positioning of the lens onto the eyeball would also be more difficult.

FIG. 1 illustrates an example of embodiment of the present invention. The illustration discloses different parts of the contact lens manipulator in a disassembled state.

A lens-fetching device 1 comprises a shaft 1b ending in a hemisphere-shaped end 1a. The shaft 1b of the lens-fetching device 1 can be parked inside an adapted bore 6 of a main body of a lens manipulator 7. The bore 6 stretches from a first end of the main manipulator body 7 from a centre location of a curved surface 2 being used when a contact lens is placed onto an eyeball. The surface 2 and the end of the main manipulator body 7 supporting the surface 2 is denoted a contact lens applicator 2.

The hemisphere-shaped part 1a of the lens-fetching device 1 is used when picking a contact lens out of a storage box. The curvature of the hemisphere is adapted to the inner surface of the contact lens body facing towards the eyeball. More details of using the contact lens manipulator according to the present invention are discussed in more detail below.

The other end of the main manipulator body 7 opposite the contact lens applicator 2 is supporting a pincer 3 with a first gripping arm 3a and a second gripping arm 3b. The bore 6 stretches through the longitudinal axis of the main manipulator body 7 and ends up in a joining surface 3c of the main manipulator body 7 located in between the first gripping arm 3a and the second gripping arm 3b.

The free end of the first gripping arm 3a and the second gripping arm 3b is curved outwardly as seen from the main manipulator body 7 forming lip-shaped endings of the free parts of the two gripping arms. The shaping is designed to provide a gentle contact surface between the free ends of the gripping arms when the pincer 3 is used to remove a contact lens from an eyeball. The lowest parts of the curved lips of the free ends are smooth and slippery avoiding any damage to the eyeball when brought in contact with the surface of the eyeball. A little bit further upwards the lip surface on a side of the lips facing inwards into the gap between the first and second gripping arms 3a, 3b, there can be optionally arranged a section providing some slight friction (for example tiny grooves) which facilitate releasing the contact lens from the eyeball when the pincer 3 is operated.

When the lens-fetching device 1 is inserted into the main body of the main manipulator body 7, into the bore 6, the shaft 1b of the lens-fetching device 1 is protruding outside the joining surface 3c in between the first gripping arm 3a and the second gripping arm 3b.

Figure 2:
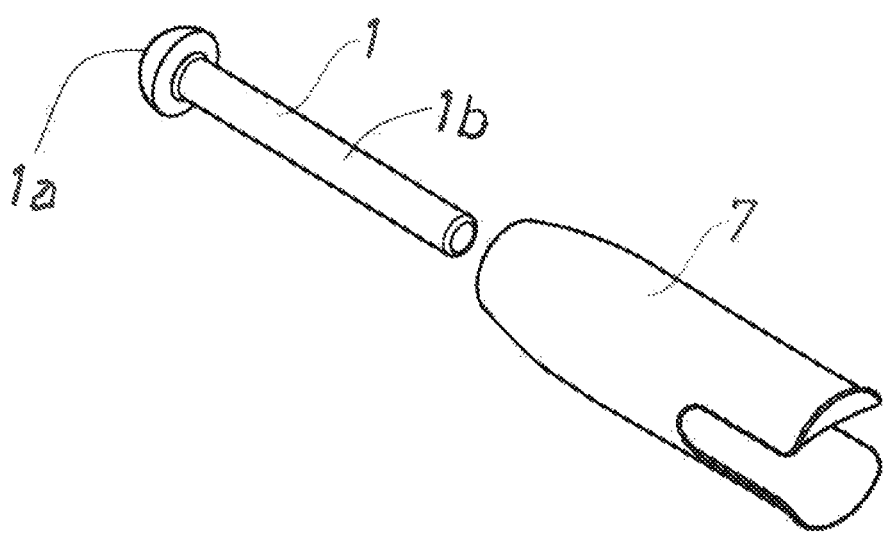
FIG. 2 illustrates details of the example of embodiment illustrated in FIG. 1.

FIG. 2 discloses the relationship between the lens-fetching device 1 and the main manipulator body 7 when viewed from another angle.

Figure 3:
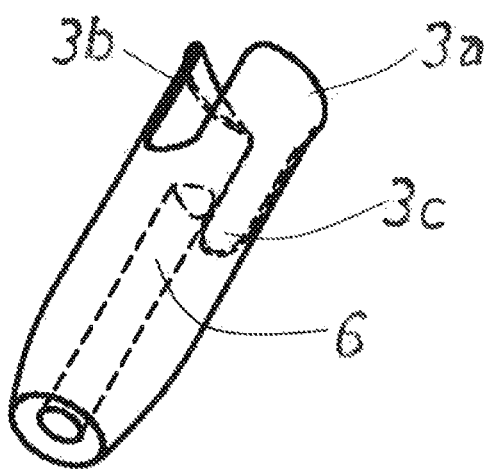
FIG. 3 illustrates further details of the example of embodiment illustrated in FIG. 1.

FIG. 3 discloses a "see-through" illustration of the main manipulator body 7. The bore 6 is visible as stippled lines.

Figure 4:
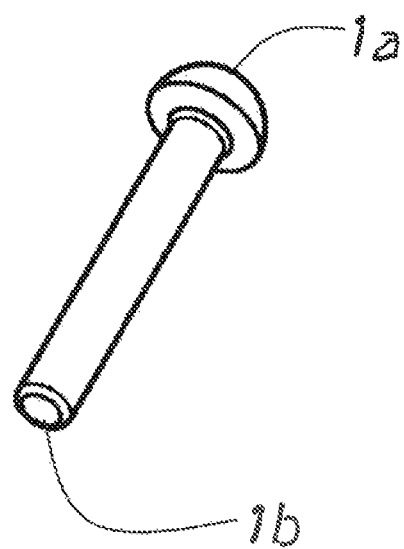
FIG. 4 illustrates an example of embodiment of the present invention.

FIG. 4 illustrates the lens-fetching device 1 with the hemisphere-shaped end 1a. The other end of the lens-fetching device is the end that is inserted into the bore 6 of the main manipulator body 7. The length of the shaft 1b is adapted to the length of the bore 6 with some additional length extending the total length of the shaft 1b to be longer than the length of the longitudinal bore 6 of the main manipulator body 7.

When the shaft 1b of the lens-fetching device 1 is parked inside the bore 6 of the main manipulator body 7, the end of the shaft is protruding outside the joining surface 3c in between the gripping arms 3a and 3b as disclosed above. The outside protruding part of the shaft 1b is protruding long enough to allow the end 1b to be contacted with a finger or a pencil, or any other object operated manually. The extra protruding part of the shaft 1b enables a possible operation of manually pushing the lens-fetching device 1 out of the bore 6 such that the hemisphere-shaped part 1a of the lens-fetching device 1 is moving away from the surface of the lens applicator 2. Therefore, the total length of the shaft 1b is adapted to be:

a) long enough to protrude outside the joining surface 3c in between the gripping arms 3a, 3b, and b) when pushed outwardly with a manual pushing of the end of the shaft 1b being located at the pincer side of main manipulator body 7, the length of the shaft 1b being exposed due to the manual pushing operation, located between the surface 2 of the main manipulator body 7 and the hemisphere-shaped part 1a of the lens-fetching device 1, has to be long enough to allow fingers of a user to grip around the shaft 1b without the fingers contacting either of the surfaces of the hemisphere-shaped part 1a of the lens-fetching device 1 and the surface 2 of the main manipulator body 7.

Further, these length requirements of the shaft 1b of the lens-fetching device 1 also define the dimensional properties of the longitudinal length of the main manipulator body 7.

Figure 5:
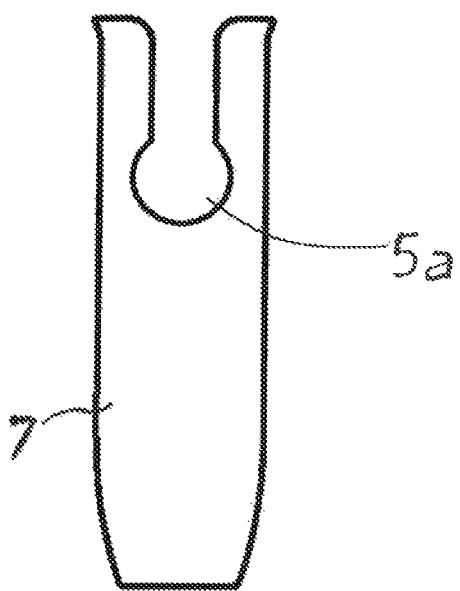
FIG. 5 illustrates another example of an embodiment of the present invention.

FIG. 5 illustrates an example of embodiment of the present invention wherein a circle-shaped cutting 5a is arranged where the shaft of the lens-fetching device 1 is protruding outside between the arms of the pincer part 3. This facilitates inserting a finger when engaging the shaft of the lens-fetching device 1.

Figure 6:
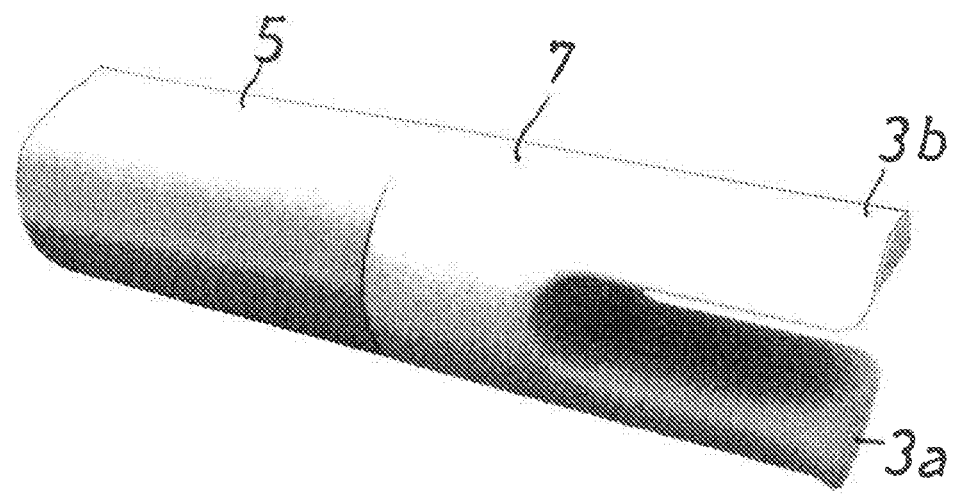
FIG. 6 illustrates an embodiment of the lens applicator/remover assembly device according to the invention.
Figure 7:
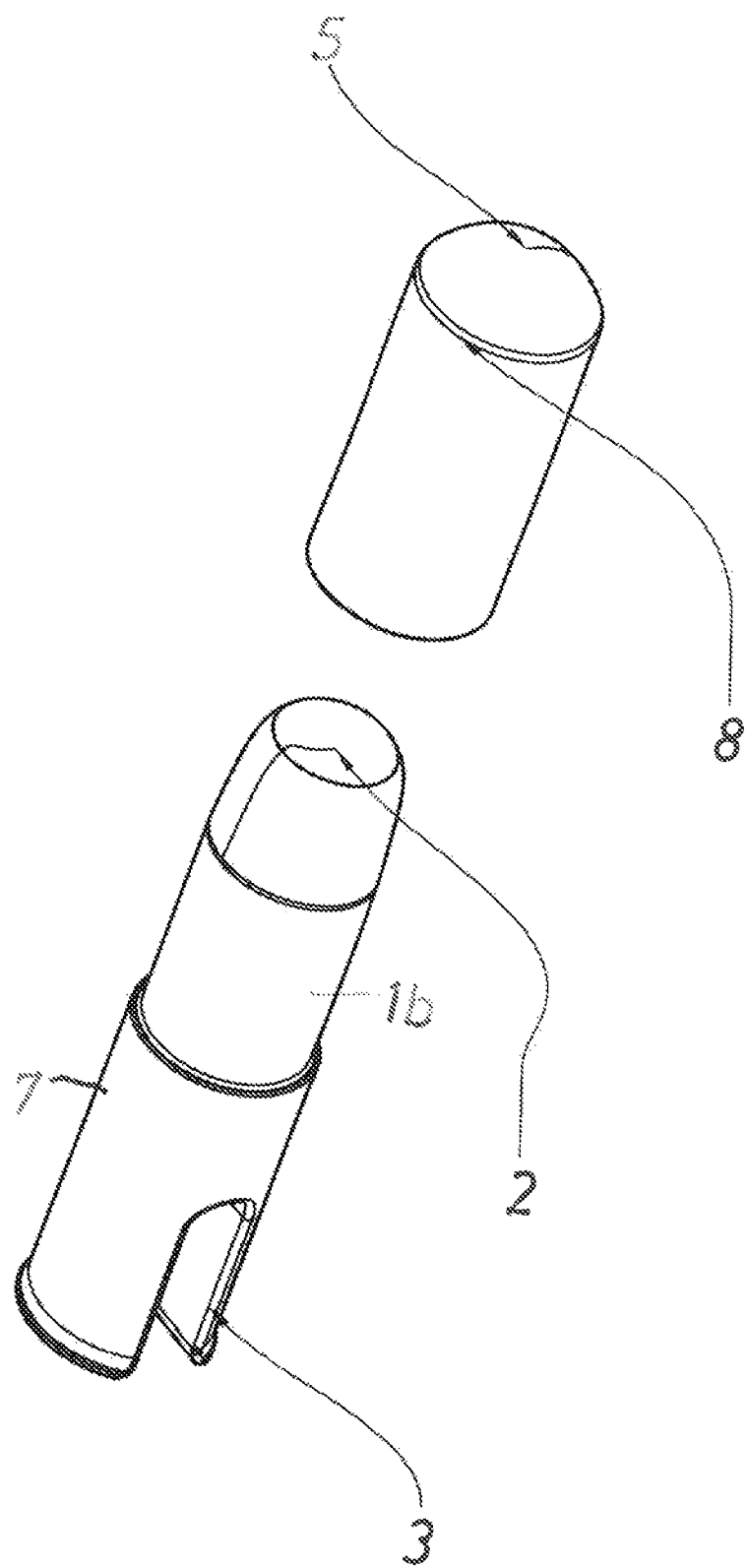
FIG. 7 illustrates an alternative embodiment of the assembly device shown in FIG. 6.
Figure 8:
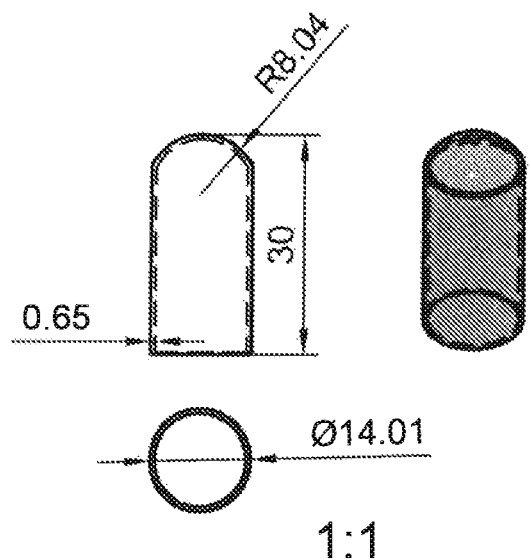
FIGS. 8-12 illustrate an embodiment of the contact lens applicator/remover device according to the invention and the assembly thereof.
Figure 8:
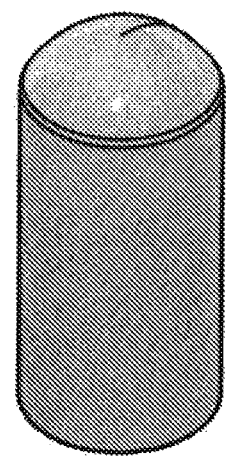

FIGS. 6 and 7 depict an alternative embodiment of the device assembly according to the present invention. In the embodiment shown in FIGS. 6 and 7 the shaft 1b of the lens-fetching device is comprised of a cylindrical element 1b fitting inside the main applicator body 7. The function of this cylindrical element 1b is the same as the piston 1b in the embodiment shown in FIGS. 1-5, i.e. transferring the contact lens from the lens pick-up section to the lens applicator section 2. In this embodiment the lens-fetching section is housed inside the part 5 of the assembly, and this lens pick-up section is covered by a lid 8 to avoid contamination of the contact lens when carried by the pick-up device as well as the pick-up device per se when the assembly according to the invention is not being used.

FIGS. 8-12 show an embodiment of the contact lens remover/applicator in true size or in enlarged or reduced size, wherein the size reduction or enlargement is indicated in the figures as ratios. The sign Ø relates to the diameter of a circle or curve and the sign R relates to the radius of a circle or curve. All the numbers provided in the FIGS. 8-12 relate to mm (except where the numbers are parts of a ratio).

In a preferred embodiment of the present invention the material used when manufacturing the lens-fetching device 1 is plastic while the preferred material of the main body of the main manipulator body 7 is silicon. For ensuring aseptic surfaces of the assembly according to the invention it is also possible to apply an antiseptic lubrication onto the surfaces of the device coming into contact with the relevant contact lens. Such an antiseptic lubrication should not be irritable to the eye or could be a fluid that may be neutralized shortly or the lens is to be picked up or placed onto the eye. Such substances or liquids are known to the person skilled in the art and may comprise systems already used within the ophthalmic industry. One example of such a system is the hydrogen peroxide/catalase system used conventionally for storing soft and hard contact lenses.

In examples of embodiments as for example disclosed in FIG. 5, it is possible to increase the mechanical integrity of the pincer arms 3a and 3b by incorporating an adapted metal shirt inside the bodies of the pincer arms 3a and 3b.

Another form factor that may be taken into account when making a pincer 3 according to the present invention is to adapt the longitudinal running opening between the first gripping arm 3a and the second gripping arm 3b to the typical dimension of a human eye. When operating the pincer 3, the first gripping arm 3a and the second gripping arm 3b should be placed in contact with the eyeball on respectively a left-hand side and a right-hand side of the eyeball as seen towards the eyeball from the outside. Then the upper and lower eyelashes of the eye will be movable located in the adapted running opening between the gripping arms. Further, this arrangement and use of the pincer 3 ensure that the operation of the pincer 3 does not interfere with the user's visual eyesight.

It is further preferred that the contact lens material is a soft optical grade material. It is within the scope of the present invention, enabling manipulation of contact lenses of stiffer optical grade materials with a contact lens manipulator assembly according to the present invention.

When using a contact lens manipulator assembly according to the present invention, when placing a contact lens onto a human eyeball, it is required that the concave side of the contact lens is placed against the cornea of the eye.

The assembly comprises a lens-fetching device 1, a lens applicator 2 arranged in a first end of the main manipulator body 7, a pincer 3 arranged in a second end opposite the first end of the main manipulator body 7.

A user, when placing a contact lens onto an eyeball, performs the following steps:
  removing the lens fetching device 1 from a bore 6 arranged in a longitudinal direction of the main manipulator body 7 by pushing a shaft 1b of the lens-fetching device 1 out of the bore 6 by manually pushing the shaft 1b from the pincer 3 side of the main manipulator body,
  when the shaft 1b is sufficiently extending out away from the lens applicator 2, gripping the shaft 1b of the lens-fetching device 1 with at least two fingers of a first hand without contacting any surface of the main manipulator body 7 and the hemisphere-shaped part 1a of the lens-fetching device 1 with the fingers, or any other fingers,
  open a storage box housing a contact lens body to be applied onto an eyeball,
  place a hemisphere-shaped part 1a of the lens-fetching device 1 in contact with a surface of the contact lens facing upwards inside the storage box,
  remove the contact lens from the storage box with the lens-fetching device 1,
  gripping the main manipulator body 7 with a second hand, and
  transfer the contact lens body from the hemisphere-shaped part 1a of the lens-fetching device 1 kept in the first hand towards the surface of the lens applicator part 2 of the main manipulator body 7,
  apply the lens applicator part 2 in operational contact with the eyeball receiving the lens and release the lens onto the surface of the eyeball, and
  optionally assemble and store the contact lens manipulator assembly in a storage container.

When using a contact lens manipulator assembly according to the present invention, when removing a contact lens from a human eyeball, the pincher section 3a,3b of the applicator assembly is used.

The assembly comprises a lens-fetching device 1, a lens applicator 2 arranged in a first end of the main manipulator body 7, a pincer 3 arranged in a second end opposite the first end of the main manipulator body 7.

A user when removing a contact lens from an eyeball performs the following steps:
  removing the lens-fetching device 1 from a bore 6 arranged in a longitudinal direction of the main manipulator body 7 by pushing a shaft 1b of the lens-fetching device 1 out of the bore 6 by manually pushing the shaft 1b from the pincer 3 side of the main manipulator body, when the shaft 1*b* is sufficiently extending out away from the lens applicator 2, gripping the shaft 1*b* of the lens-fetching device 1 with at least two fingers of a first hand without contacting any surface of the main manipulator body 7 and the hemisphere-shaped part 1*a* of the lens-fetching device 1 with the fingers, or any other fingers, open a storage box to be used when storing the contact lens body to be removed from the eyeball, gripping the main manipulator body 7 with a second hand and place the pincer 3 in operational contact with the contact lens on the eyeball, and remove the contact lens from the eyeball with the pincer 3, and transfer the contact lens body from the pincer 3 to the hemisphere-shaped part 1*a* of the lens-fetching device 1 kept in the first hand, placing and releasing the contact lens body inside the storage box and close the box, and optionally assemble and store the contact lens manipulator assembly in a storage container, or optionally throwing the used contact lens body into a dustbin.

EXAMPLES

Example 1

Figure 9:
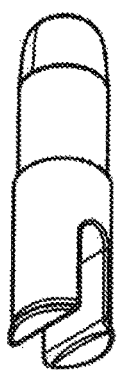
Figure 9:
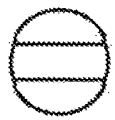
Figure 9:
Figure 9:
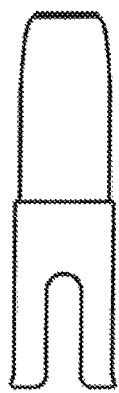
Figure 9:
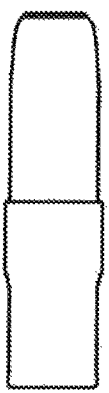
Figure 9:
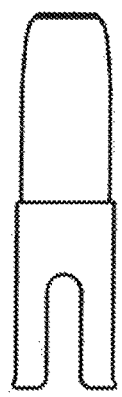
Figure 9:
Figure 9:
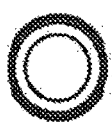
Figure 9:
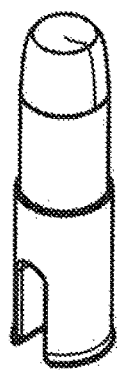
Figure 10:
Figure 10:
Figure 10:
Figure 10:
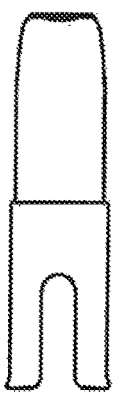
Figure 10:
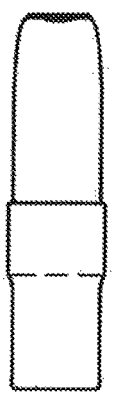
Figure 10:
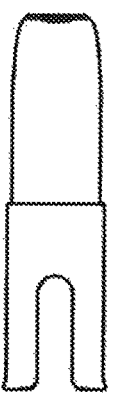
Figure 10:
Figure 10:
Figure 10:
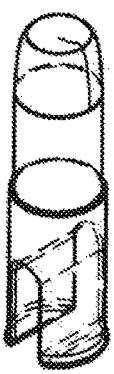
Figure 11:
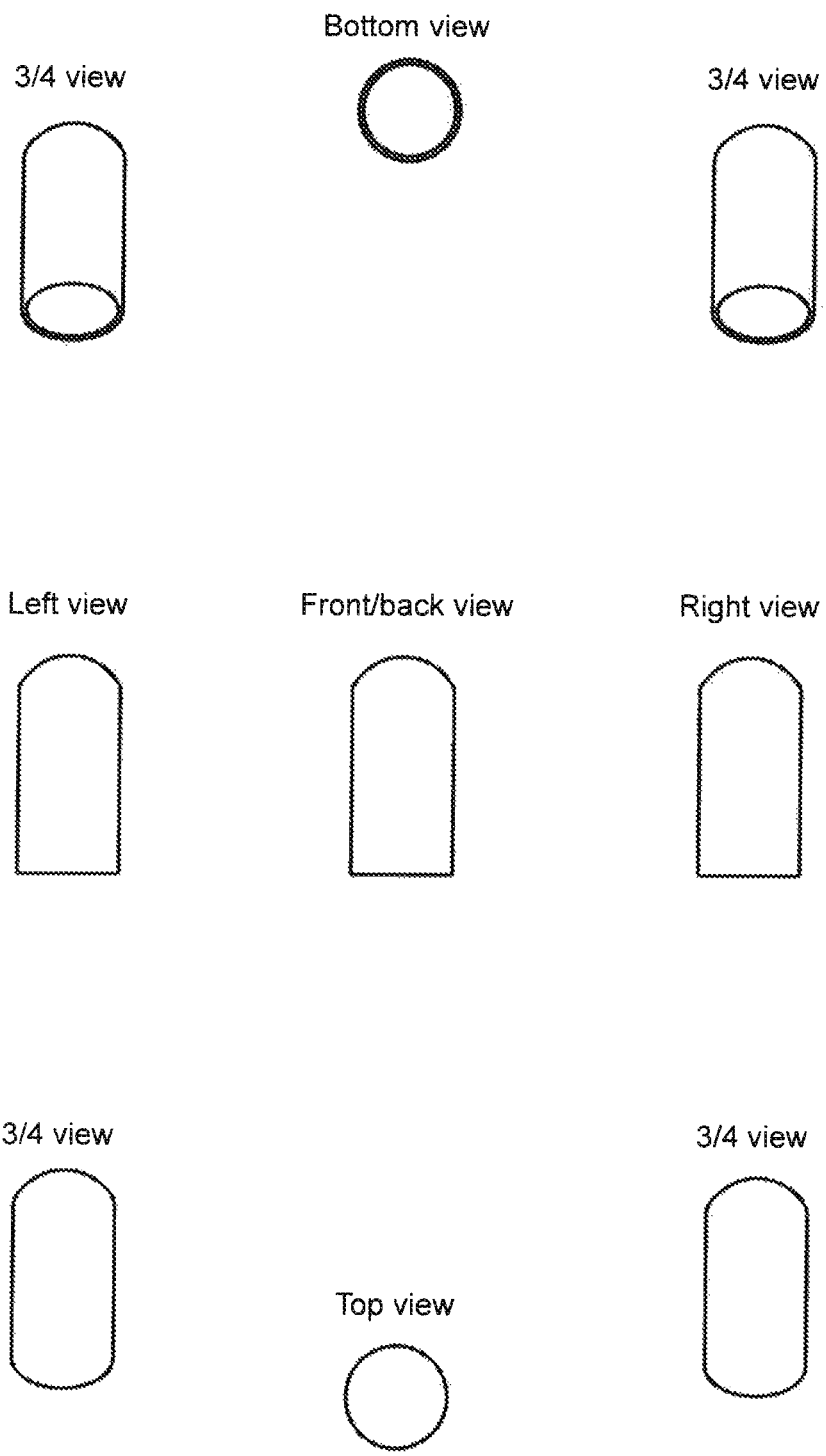
Figure 12:
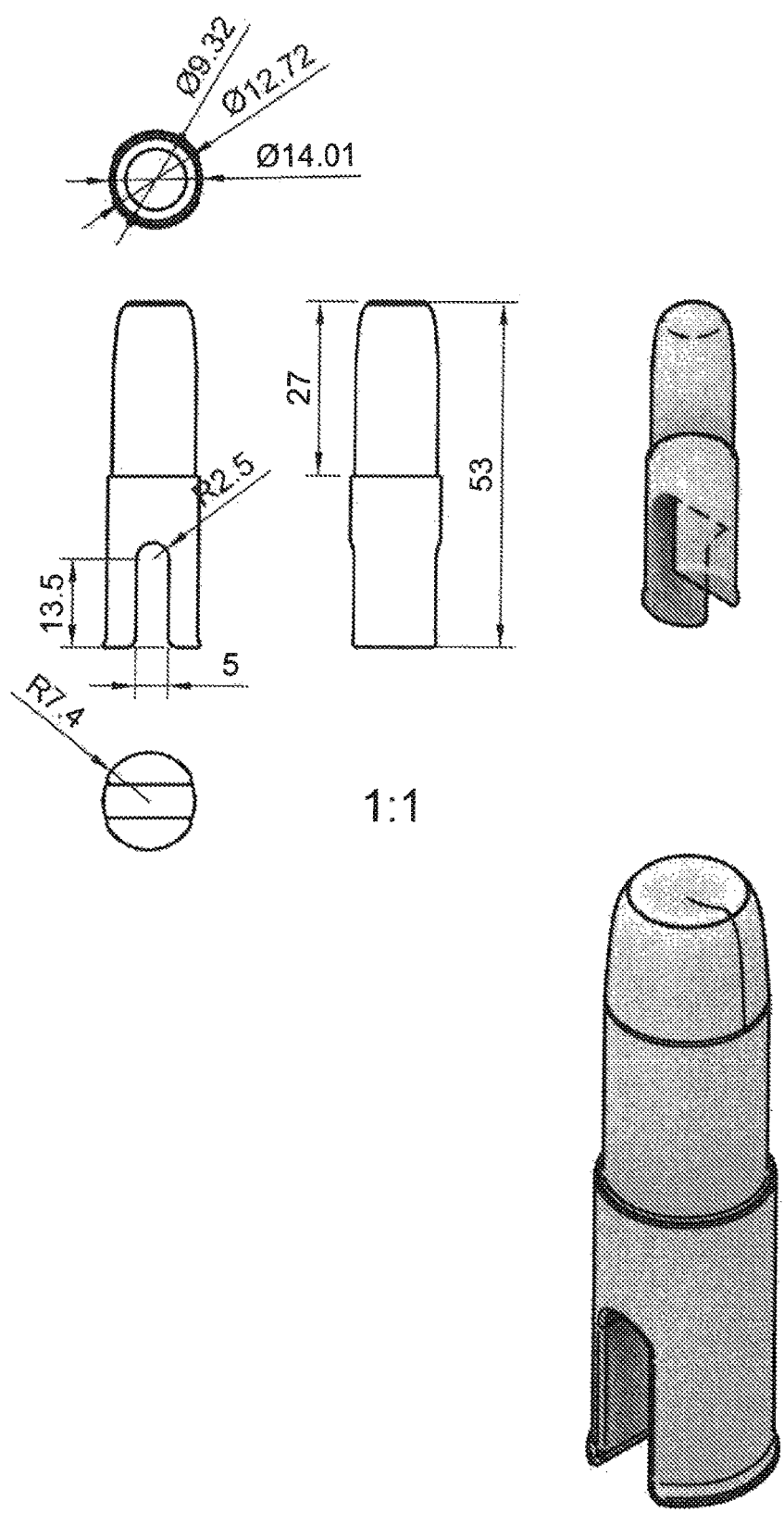

This example relates to the embodiment of the contact lens applicator/remover device according to the invention depicted in FIGS. 8-12. In these figures the assembly of the device is shown as well as the true size or in enlarged or reduced size, wherein the size reduction or enlargement is indicated in the figures as ratios. The sign Ø relates to the diameter of a circle or curve and the sign R relates to the radius of a circle or a curve. All the numbers provided in the FIGS. 8-12 relate to mm (except where the numbers are parts of a ratio). FIG. 9 shows the embodiment of the contact lens inserter/remover without hidden edges, whereas FIG. 10 shows the embodiment of the contact lens inserter/remover with hidden edges indicated in dotted lines.

The invention claimed is:

1. A contact lens manipulator assembly comprising: a main manipulator body arranged with a lens applicator in a first end of the main manipulator body, and a pincer in a second end of the main manipulator body opposite the first end, wherein a lens-fetching device comprising an outwardly shaped hemisphere part located on a first end of a shaft, wherein a second end of the shaft opposite the hemisphere-shaped part is adapted to be releasable inserted into a bore arranged in a longitudinal direction of the main manipulator body, wherein the bore is arranged from a centre point on a curved surface of the lens applicator facing outwardly through the main manipulator body to a centre point on a joining surface of the main manipulator body in between a first gripping arm and a second gripping arm of the pincer, wherein free ends of the first and second gripping arm are arranged with a lip-shaped contact surface engaging an eyeball when the pincer is operated, wherein the lips bend outwardly from the main manipulator body.

2. The lens manipulator assembly according to claim 1, wherein the hemisphere-shaped part of the lens-fetching device is adapted to a curvature of an inner surface of a contact lens body engaging an outer surface of an eyeball when the contact lens body is applied onto the eyeball.

3. The lens manipulator assembly according to claim 2, wherein the contact lens body is made from a soft optical grade material.

4. The lens manipulator assembly according to claim 3, wherein the contact lens body is made from a stiffer optical grade material.

5. The lens manipulator assembly according to claim 1, wherein a surface of the lens applicator is curved inwards into the main manipulator body, wherein a curvature of the surface is adapted to the shape of an outer surface of a contact lens body, wherein the outer surface of the contact lens body is adapted to optically correct the eyesight of a human eye on which the contact lens body is applied.

6. The lens manipulator assembly according to claim 1, wherein the length of the shaft of the lens-fetching device is long enough to protrude out from the joining surface of the main manipulator body.

7. The lens manipulator assembly according to claim 6, wherein the length of the shaft of the lens-fetching device is adapted such that a first end of the shaft is configured to protrude out from a surface on the first end of the manipulator body, when a second end of the shaft is level with the joining surface with an amount permitting human fingers to grip around the protruding part of the first end of the shaft.

8. The lens manipulator assembly according to claim 1, wherein a longitudinal opening between the first gripping arm and the second gripping arm is adapted to the dimensions of a human eye when the pincer is brought into operational contact with the eye.

9. The lens manipulator assembly according to claim 1, wherein the joining surface between the first and second gripping arms are shaped as a semicircle with a diameter adapted to an average human finger size.

10. The lens manipulator assembly according to claim 1, wherein the lens-fetching device is manufactured from plastic.

11. The lens manipulator assembly according to claim 1, wherein the main manipulator body is manufactured from silicon.

12. The lens manipulator assembly according to claim 11, wherein the gripping arms of the pincer can be reinforced with optional embedded metal parts inside the silicon.

13. The lens manipulator assembly according to claim 1, wherein surfaces of the lips on the free ends of the first and second gripping arms facing inwardly towards a gap in between the gripping arms, are arranged with grooves located above and away from the surface of the lips engaging the eyeball surface.

14. A method of placing a contact lens onto a human eyeball using a contact manipulator assembly comprising:

removing a lens-fetching device from a bore arranged in a longitudinal direction of a main manipulator body by pushing a shaft of the lens-fetching device out of the bore by manually pushing the shaft from a pincer side of the main manipulator body, when the shaft is sufficiently extending out away from the lens applicator, gripping the shaft of the lens-fetching device with at least two fingers of a first hand without contacting any surface of the main manipulator body and a hemisphere-shaped part of the lens-fetching device with the fingers, or any other fingers, opening a storage box housing a contact lens body to be applied onto an eyeball, placing the hemisphere-shaped part of the lens-fetching device in contact with a surface of the contact lens facing upwards inside the storage box, removing the contact lens from the storage box with the lens-fetching device, gripping the main manipulator body with a second hand, and transferring the contact lens body from the hemisphere-shaped part of the lens-fetching device kept in the first hand towards the surface of the lens applicator part of the main manipulator body, applying the lens applicator part in operational contact with the eyeball receiving the lens and release the lens onto the surface of the eyeball, and optionally assembling and storing the contact lens manipulator assembly in a storage container.

15. A method of removing a contact lens from a human eyeball using a contact manipulator assembly comprising:

removing the lens-fetching device from the bore arranged in the longitudinal direction of the main manipulator body by pushing the shaft of the lens-fetching device out of the bore by manually pushing the shaft from the pincer side of the main manipulator body, when the shaft is sufficiently extending out away from the lens applicator, gripping the shaft of the lens-fetching device with at least two fingers of a first hand without contacting any surface of the main manipulator body and the hemisphere-shaped part of the lens-fetching device with the fingers, or any other fingers, open a storage box to be used when storing the contact lens body to be removed from the eyeball, gripping the main manipulator body with a second hand and place the pincer in operational contact with the contact lens on the eyeball and remove the contact lens from the eyeball with the pincer, and transfer the contact lens body from the pincer to the hemisphere-shaped part of the lens-fetching device kept in the first hand, and placing and releasing the contact lens body inside the storage box and close the box, and optionally assemble and store the contact lens manipulator assembly in a storage container.

16. The method according to claim 15, wherein placing the removed contact lens body in the storage box is replaced by placing the removed contact lens body in a dustbin.

* * * * *